United States Patent [19]

Allington et al.

[11] Patent Number: 4,781,464

[45] Date of Patent: Nov. 1, 1988

[54] GEL SCANNER

[75] Inventors: Robert W. Allington; Wylee D. Brunken, both of Lincoln; Lawrence L. Sedlak, Dwight, all of Nebr.

[73] Assignee: Isco, Inc., Lincoln, Nebr.

[21] Appl. No.: 851,233

[22] Filed: Apr. 14, 1986

[51] Int. Cl.$^4$ .................. G01O 3/51; G01N 21/86
[52] U.S. Cl. ...................... 356/419; 356/435; 356/444
[58] Field of Search ............... 356/72, 73, 435, 444, 356/407, 419, 244

[56] References Cited

U.S. PATENT DOCUMENTS

| | | | |
|---|---|---|---|
| 3,994,593 | 11/1976 | Kato et al. | 356/444 |
| 4,195,932 | 4/1980 | Popelka | 356/407 |
| 4,266,872 | 5/1981 | Mitsuhashi | 356/244 X |

FOREIGN PATENT DOCUMENTS 59-52235  3/1984  Japan .................. 356/444

*Primary Examiner*—Vincent P. McGraw
*Attorney, Agent, or Firm*—Vincent L. Carney

[57] ABSTRACT

To scan gels optically, a gel scanner includes a gel holder and an optical system mounted for motion with respect to each other. The optical system includes a tungsten halogen lamp, first aperture, second aperture, beam splitter and first and second light paths; the first aperture having a dimension in the direction of motion of the gel with respect to the optical system of less than 0.5 millimeter and a dimension in a direction transverse to the direction of motion of less than 10 millimeters. The lamp and first aperture are mounted on one side of said gel holder and the second aperture is mounted on the other side of said gel holder. The beam splitter transmits light in a first direction along the first light path and in a second direction along a second light path with the: (1) first light path including a first photodetector and an interference filter for passing light within the range of 400 nanometers wavelength to 700 nanometers wavelength to it; and (2) the second light path having a second photodetector.

19 Claims, 2 Drawing Sheets

GEL SCANNER

BACKGROUND OF THE INVENTION

This invention relates to gel electrophoresis and more particularly to methods and apparatuses for detecting bands in gels, such as for example gel scanners.

In one class of gel scanner, bands representing molecular species that have been resolved in the gel by electrophoresis are detected optically by determining the amount of certain frequencies of light that are absorbed by the band. The absorption of light is aided by staining the bands. This class of gel scanner includes at least one light source and a photodetector. Commonly, a filter is used to select the frequency of light absorbed by the bands. A reference signal is obtained from a photocell responding to light which is not subject to absorption by the bands that have been resolved within the gel before being transmitted to the photocell.

In one prior art gel scanner of this type, one light beam is transmitted through the gel to detect bands and a second beam of light is transmitted through gel in which there are no bands. The two beams of light are detected by photocells and the signals from them compared to determine when light has been absorbed by a band of molecular species being resolved in the gel.

This prior art gel scanner has a disadvantage in that its sensitivity or its ability to differentiate bands from gel is adversely affected by background such as by bubbles in the gel which background may be different in the area through which the sensing beam of light passes and the area through which the reference beam passes.

In another type of prior art photometric device, two different narrow bandwidth frequencies of light are used. One frequency is within the range that is absorbed by the sample and the other is not in that range. The two frequencies are applied together to the sample to make the measurement and then separated, with one of the frequencies being used as the sensing frequency and the other being used as a reference frequency to remove background noise.

This type of prior art photometric device has a disadvantage in that it is expensive, inconvenient to use, and under some circumstances provides a substantial amount of nonlinearity.

The deficiencies of prior art gel scanners have been so large that they have not generally been used to scan silver stained gels. Silver stained gels have been photographed instead. This is time consuming and furthermore destroys some of the high sensitivity which is the principal advantage of silver staining conventional stains. The difficulty in scanning silver stained gels arises from the fact that silver stains do not produce light absorbance bands of narrow wavelength or frequency bandwidth. In fact, they are brown in color.

Photography can cope with this since photographs can be made with the gel backilluminated with a physically broad, spatially uniform light source that lessens the photometric effect of gel imperfections, such as bubbles. On the other hand, direct scanning of the gel must necessarily use a narrow, collimated light source, such as through pairs of slits. Because of the broad wavelength bandwidth of absorbance of silver stains, the usual signal-to-noise improvement method of using a narrow sensing wavelength bandwidth won't work since it responds only to a small part of the total absorbance. On the otherhand, this bandwidth can't be sufficiently increased without prohibitive linearity problems. In the subject invention, this problem is solved by using a broad bandwidth of reference wavelengths.

SUMMARY OF THE INVENTION

It is an object of the invention to provide a novel method and apparatus for scanning gels.

It is a further object of the invention to provide a novel optical sensing means which is better able to eliminate background noise.

It is a still further object of the invention to provide a novel gel scanner in which light is transmitted through the gel and a frequency of visible light within the absorbance spectrum of the band separated from other light as the sensing light with at least some of the other light being the reference light.

It is a still further object of the invention to provide a novel gel scanner with superior linearity.

In accordance with the above and further objects of the invention, light is applied across an area of the gel to sense bands of different molecular species within the gel. The frequencies of light which are used to sense the molecular species are applied to one photocell and other frequencies to a different photocell. The signals generated by the two photocells are compared to obtain a signal representing the light absorbance of the area being scanned. Absorbance is defined as the negative logarithm of the ratio of light intensity leaving the gel to the light intensity entering the gel.

In one embodiment, the frequency of light which is to be transmitted to the sensing photocell is separated from the other frequencies of light passing through the gel. Advantageously, an interference filter having near-zero reflectivity in a narrow bandwidth of the predetermined selected frequency is used, with light passing through the interference filter being sensed by a sensing photocell and at least a portion of the light of other frequencies being sensed by a reference photocell. Surprisingly, the use of a wide band of frequencies in the reference light increases linearity of the measurements.

It is believed the use of a wide band increases linearity because, as the concentration of the molecular species increases, the absorbance of light of the frequency selected increases in accordance with Beer's Law but this light is only a portion of the light within the most efficient portion of the absorption spectra of the bands because a narrower bandwidth is selected for sensing than the bandwidth of the absorption spectra of the band. The frequencies of light used as the reference light includes frequencies which are absorbed as well as frequencies which are not absorbed. As the absorbance increases, the absorbed frequencies decrease in intensity, decreasing the amount of light reaching the reference photocell. At these high absorbances at which the measuring photocell would start to show a non-linear response, light of non-absorbed frequencies is so much greater in intensity at the reference photocell than light of absorbed frequencies, the reference photocell response stops decreasing. This compensates for the onset of nonlinearity of the measuring photocell.

In another embodiment of the invention, light is transmitted from a single source through the gel, with a portion of the light being passed through an interference filter to represent the sensing frequency and a part transmitted through another filter to the reference photocell. The filter which selects a band to be applied to the sensing photocell selects those frequencies which are in the visible range and within the absorbance spectra of the bands and the light which is applied to the reference photocell is infrared plus other light selected by the other filter because it is not absorbed to a great extent by the gel.

Generally, this gel electrophoresis scanning technique is used with dyed gels and the absorption spectra is selected within the visible range to permit visual operation of the resolution of the bands. One type of dye for such staining is Coomassie Brilliant Blue and another is a silver stain. The embodiment using the light reflected from the interference filter is suitable for stains like Coomassie Brilliant Blue because of their narrow band of absorbed light frequencies. The infrared selected reference light provides greater differentiation of the bands especially with silver stained gels, because the infrared light is not affected by the silver stained gel as much as other light and because the absorbance of silver stained gels is very broad in wavelength; the bands appear brown rather than a chromatic color.

As can be understood from the above description, the gel scanner of this invention has several advantages such as: (1) it is more linear in operation as the concentration of the band to be detected increases; and (2) it removes background noise more effectively and thus increases the ability of the scanner to detect bands.

DESCRIPTION OF THE DRAWINGS

The above noted and other features of the invention will be better understood from the following detailed description when considered with reference to the accompanying drawings in which.

DETAILED DESCRIPTION

Figure 1:
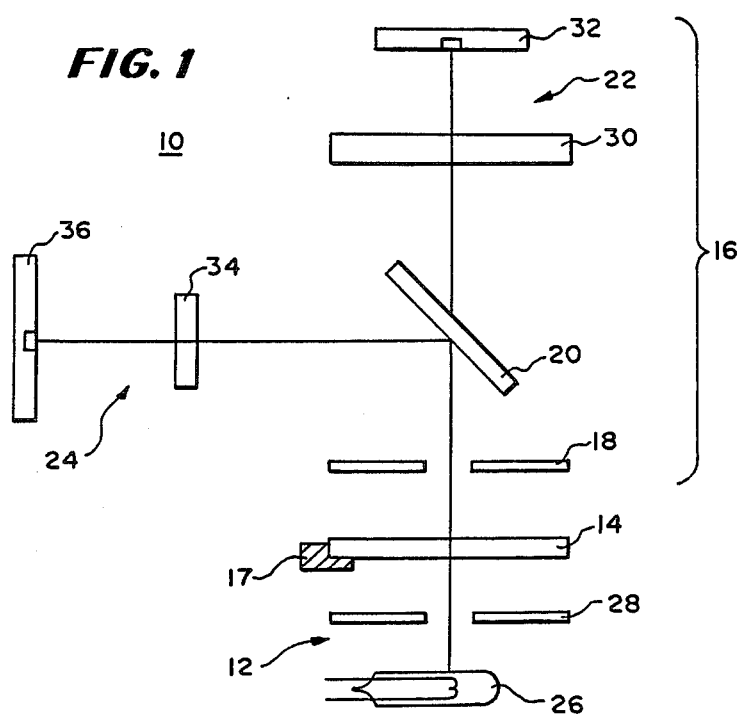
FIG. 1 is a schematic diagram of an optical system in an embodiment of the invention.

In FIG. 1, there is shown a schematic diagram of an optical system 10 having a light source 12, a gel sample 14, and a signal detection system 16. This optical system provides unusually good signal-to-noise ratio (e.g. freedom from responses to extraneous gel characteristics such as bubbles) when scanning silver stained gels, or other gels stained with another stain also procuing a broad wavelength region of absorbance. The light source 12 transmits a scanning beam of light through the gel 14 as the optical system is moved with respect to the gel 14, located in a cuvette or gel holder, having walls capable of passing light. The signal detection system 16 receives the light after it passes through the gel 14 and selects a measuring beam and reference beam from it for comparison to generate a signal indicating bands in the gel 14. While the optical system is moved in the preferred embodiment, it is of course possible to move the gel instead or both since relative motion between the two is all that is required.

To sense the optical signals, the signal detection system 16 includes an aperture plate 18, a beam splitter 20, a sensing system 22, and a reference system 24. The beam splitter 20 receives light from the gel 14 after it passes through the aperture plate 18 and transmits a portion of it to the sensing system 22 to sense frequencies of light and a portion to the reference system 24 after the light has been transmitted through the same area of the gel 14. Some of the light to be used for sensing bands is absorbed by the bands, if there are any bands, but a much lower portion of the light used for the reference is absorbed by the bands. The sensing signal is compared to the reference signal to cancel background noise in the gel 14 such as caused by bubbles or the like and detect the light absorbance of the bands.

To provide light suitable for the optical system 10, the light source 12 includes a tungsten halogen lamp 26 and an aperture plate 28. The aperture plate 28 is between the lamp 26 and the gel 14 and includes within it a 0.15 mm (millimeter) by 3.3 mm slot with the 3.3 mm dimension being positioned perpendicular to the line of motion of scanning so as to line up with bands and the 0.15 mm slot to be in a direction aligned with the direction of motion between the optical system 10 and the gel 14. In the preferred embodiment, the lamp is a General Electric type 773 lamp.

To reduce stray light in the signal, the slot is intended to be smaller in size than the bands which are to be detected and preferably, will overlie only a central portion of the bands at some time during scanning. The aperture is sufficiently large to pass detectable light but less than the size of the bands.

With this arrangement, light containing a wide range of frequencies from the tungsten halogen lamp 26 is applied to the gel 14 through a slot in an aperture plate 28 sized to overlie bands of size for which detection is intended in one column of bands to detect absorbance without undue stray light. In the preferred embodiment, a single optical system is issued to sense one column at a time in the gel but a plurality of optical systems to sense side by side columns could be used if desired.

The aperture plate 18 is similar to the aperture plate 28 and directs light from the band only without substantial stray light to the beam splitter 20. In the preferred embodiment, the beam splitter 20 is an uncoated plate of very thin quartz of glass (a microscope cover slip is satisfactory). It redirects approximately 10 percent of the light into the reference system 24 and the remainder passes through the beam splitter 20 to the sensing system 22.

The sensing system 22 includes a narrow-band visible wavelength selecting filter 30 and a photocell 32 positioned so that light passing through the beam splitter 20 is filtered by the filter 30 before reaching the photocell 32. In the preferred embodiment, the filter 30 is an interference filter of less than 20 nanometers bandwidth which passes light at 580 nanometers but it is selected to transmit only light within the absorption spectrum of the bands so that the concentration of the molecular species forming a band results in a decreased mount of light being transmitted to the photocell 32 with light frequencies not within the efficient absorption spectrum of the band being blocked by the filter 30.

The reference system 24 includes an infrared filter 34 and a reference photocell 36. The infrared filter passes light having a wavelength longer than 640 nm (nanometers) and shorter than 5 microns. These ranges are ranges in which at least 90 percent of the amplitude of light in the wavelength region longer than the central wavelength of the filter 30 is attributable to the light within the bandwidth between 640 nm and 5 microns. Preferably, the infrared filter should not pass light passed by the visible light filter 30. In the preferred embodiment filter 34 is a Wratten number 35 "purple" filter that passes light in the visible range between 390 and 450 nm, absorbs light from 460 to 650 nm (this covers the passband of light filter 30) and passes light from 665 nm to 2.6 microns, the latter wavelength region being predominantly in the infrared.

Although this embodiment is primarily intended for scanning silver stained gels, the 390 to 450 passband of the Wratten number 35 filter provides improved performance with blue stained gels such as those stained with Coomassie Billiant Blue. It does not appreciably degrade the scanning of silver stained gels because the tungsten halogen lamp 26 emits much more of its light in the near infrared than it does from 390 to 450 nm.

The visible light filter 30 should pass light within a narrow band complimentary to the absorbance of the bands. This narrow band should be within a range of wavelengths of between 400 to 700 nanometers when stained gels are used. In the preferred embodiment, inteference filters are obtained from Ditric Optics, Inc. from specifications of 580 nm, 3 cavity, 9.8 nm HBW and 50 percent transmittance at 580 nm. The frequencies of the light passing through the gel to the reference photocell, include light only of frequencies not transmitted to the sensing photocell and having a bandwidth of frequencies at least 10 times wider than the bandwidth of frequencies reaching the said first photocell.

Figure 2:
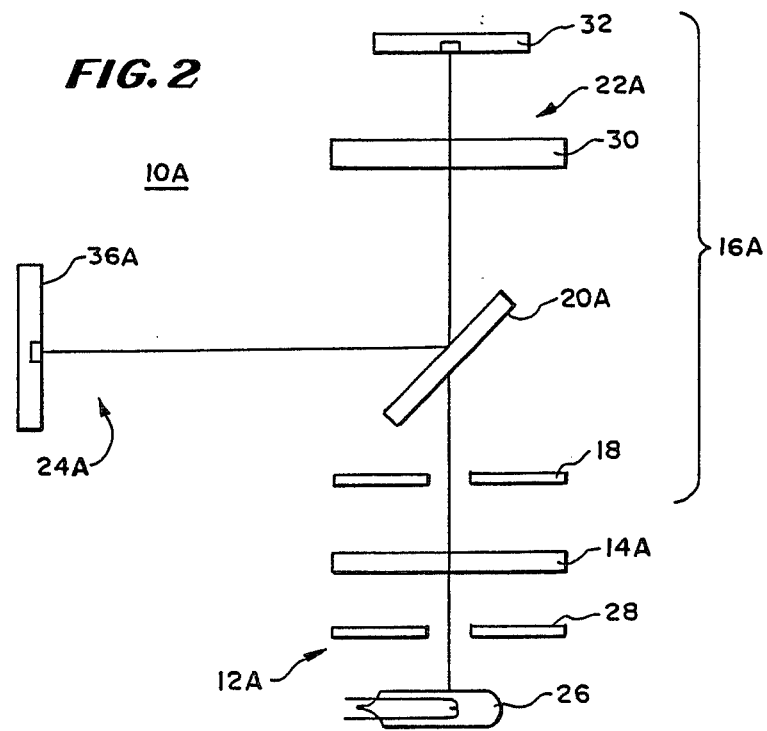
FIG. 2 is a schematic diagram of a second optical system which is an embodiment of the invention.

In FIG. 2, there is shown another embodiment of optical system 10A, similar to that of optical system 10 in FIG. 1 and having a light source 12A identical to the light source 12 in FIG. 1. It provides unusually good signal-to-noise ratio and linearity when scanning stained gels with a narrow wavelength region of absorbance such as Coomassie Brilliant Blue stained gels. In this embodiment, the gel slab 14A is substantially the same as the gel slab 14 but may be stained with any of a number of suitable stains, or be different in composition since the slab itself is not part of the invention except insofar as it cooperates with the optical system.

The signal detection system 16A is similar to the signal detection system 16 and includes the aperture plate 18 and a beam splitter 20A, a sensing system 22A and a reference system 24A. The beam splitter 20A passes light from the aperture plate 18 to the sensing system 22A which passes to the sensing photocell 32 only light which is within the pass band range of wavelengths of the interference filter 30. Light not in that range is reflected back to the beam splitter 20A which transmits it to the photocell 36A within the reference system 24A. The filter 30, passes light within the wavelength region of absorbance of the stain for the stained gel system 14A, but other frequencies of light are passed on to the photocell 36A which serves as a reference.

In this embodiment, the linearity of the signal is surprisingly good as the concentrations of the bands in the gel increase to a high level. The wide band of frequencies of light applied to the reference system 24A compensate for an increase in nonlinearity in the sensing system with increasing concentration of the bands at high concentrations, possibly because of nonlinearity of its own as the absorbed frequencies in the reference light are absorbed to the point that they become negligible compared to the reference light at absorbed frequencies.

Figure 3:
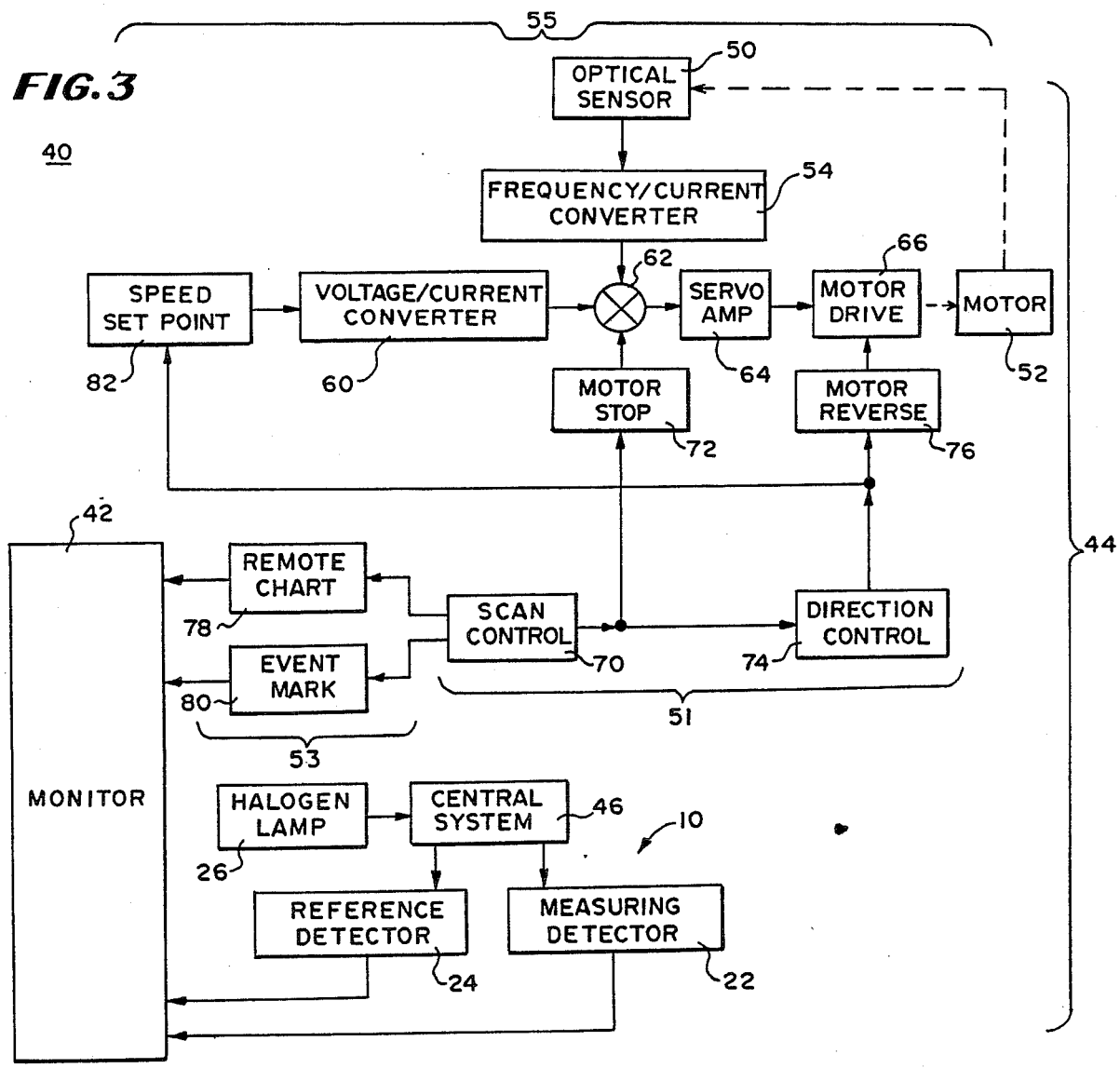
FIG. 3 is a block diagram of a system which may be used with the optical systems of FIGS. 1 or 2.

In FIG. 3, there is shown a block diagram of a gel scanner 40 with which the optical systems of FIGS. 1 and 2 may be used. As shown in FIG. 3, the gel scanner 40 is adapted to be connected to a monitor 42 and includes circuitry and equipment 44 for moving the optical system and a slab of gel with respect to each other and recording the location of bands in the gel as a result of detectionby the optical system.

The monitor 42 may be any conventional type of monitor such as those described in U.S. Pat. Nos. 3,783,276, 3,822,097 and 3,859,539. This type of equipment is available commercially and one model of monitor which is used in the preferred embodiment is sold under the designation of ISCO UA5 Absorbance Monitor by Isco, Inc. of Lincoln, Nebraska. The disclosures of the above patents and publication are incorporated herein by reference.

The optical system 10 which is mounted to a movable carriage in shown generally in FIG. 3 and has a central system 46 which includes the aperture plates 18 and 28 (FIG. 1), the beam splitter 20, the reference detector 24, measuring detector 22 and halogen lamp 26 (FIG. 1) or the corresponding parts in FIG. 2.

To control the speed and direction of the carriage which with respect to the slab in a manner known in the art, the gel scanner 40 includes a speed and direction control circuit 51, a recording control circuit 53, and a motor control circuit 55 to control a motor 52 for driving the carriage holding the optical system 10 (FIG. 1) or 10A (FIG. 2). The speed and direction control circuit 51 includes manual controls which are set to establish potentials in a resistor divider circuit. The divider circuit is electrically connected to a regulated power supply for driving the motor under the control of the motor control circuit 55 and applies signals to the monitor 42 through a recorder control circuit 53 which serves as a connection to the monitor 42.

To set the speed, the speed set point 82 includes a switch which connects different resistors to drive different potentials from a regulator in a manner known in the art or an electronic gating circuitry to interconnect the resistors in the same manner (voltage-to-current converter 60). The direction control 74 similarly includes a relay-operated or manually operated mechanical, double-pole double-throw switch which connects power to the motor drive circuit through a reversing switch to reverse the polarity at the armatures of the motor.

To drive the gel holder, the motor 52 is mechanically connected thereto to drive the gel holder in a conventional manner for a gel scanner and drives an optical tachometer connected to its output shaft. The tachometer supplies signals to the motor control 55 to form a feedback circuit for controlling the speed of the motor.

To control the speed of the motor, the motor control circuit 55 includes an optical sensor 50 which senses light pulses caused by the interruption of light from a lamp by a plastic disc mounted for rotation with the armature shaft of the motor 52. The light is interrupted at a rate proportional to the speed of the motor and thus the speed of the gel holder. The output from the optical sensor 50 is transmitted to the comparator input of the frequency-to-current converter 54. This converter generates DC current pulses proportional to the input frequency and motor speed under the control of the optical sensor 50 and supplies them to a null point for comparison with the set speed.

The voltage-to-current converter 60 and the frequency-to-current converter 54 are each electrically connected to the summing node 62 which compares the two currents and supplies a signal through a servo amplifier 64 to the motor drive circuit 66 to drive the motor so that a positive error signal results from a speed higher than the set speed, which decreases the motor speed and a negative error signal results from a speed lower than the set speed to increase the motor speed. The motor stop circuit 72 drives the set point 62 to cause the motor to stop and may initiate a switching action to reverse motor direction. This circuit includes a flip-flop which is switched at the end of a scanning run to stop the motor and reverse direction by supplying a signal to a relay operated switch in the motor reverse circuit 76.

Figure 4:
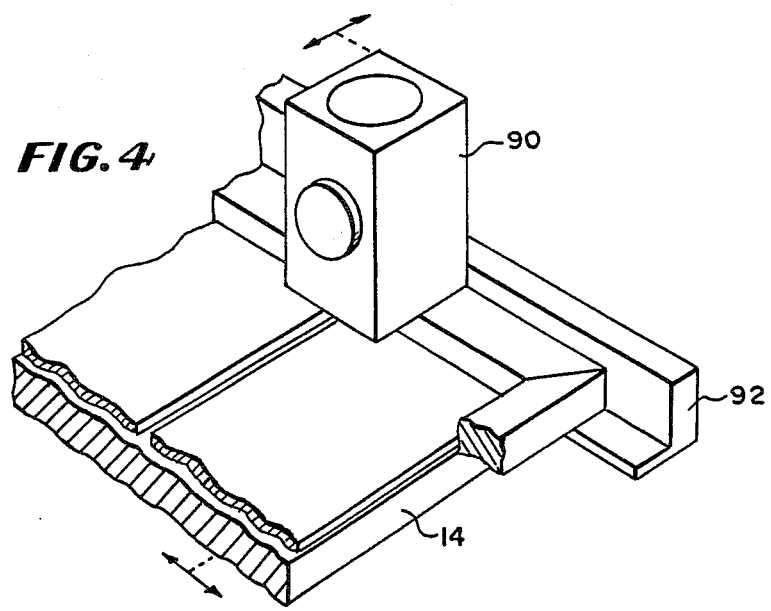
FIG. 4 is a fragmentary, simplified perspective drawing of a portion of the gel scanner of FIG. 3.

In FIG. 4, there is shown a holder 90 for mounting matched pairs of photocells, a beam splitter, and an aperture plate. The gel holder or cuvette is slideable, in the horizontal direction perpendicular to the horizontal scanning direction as noted by the arrows in FIG. 4, on fixed guides 92 to position different parallel tracks of electrophoresis gel bands within the scanning path. The halogen lamp 26 (FIG. 1) and aperture plate 28 (FIG. 1) are mounted below the gel holder and are aligned with the holder 90.

Prior to scanning, bands of molecular species are resolved in a gel in a manner known in the art. After electrophoresis in a slab to form bands and staining to increase visibility, the scan control 70 (FIG. 3) and the direction control 74 (FIG. 3) are set to cause the carriage to move back and forth across the gel while light from a tungsten halogen lamp 26 (FIG. 1) is transmitted through the gel with a selected frequency in the absorbance spectrum of the bands being transmitted to a sensing photocell 32 (FIG. 1). At least some of the remainder of the light transmitted through the gel is transmitted to a reference photocell 36. The signals from the photocells are received by a monitor 42 (FIG. 3) which compares them and transmits a resulting signal equal to the absorbance difference between the measuring and reference light to a chart recorder to record the location of the bands.

The gels are stained with materials that have an affinity for proteins in the gels and thus render the bands visible. Staining with silver and Coomassie Brilliant Blue are described in "A Highly Sensitive Silver Stain for Detecting Proteins and Peptides in Polyacrylamide Gels", Switzer, III, Robert C., Merril, Carl R. and Shefrin, Sidney (1979), *Analytical Biochemistry*, Volume 98, n.1 Sept. 15, 1979; and "A Sensitive Procedure for Silver Staining Proteins in Agarose Gels", Peats, Stephen (1983) BioTechniques, 156, September/October 1983.

To set the speed, a voltage divider is selected in the scan control 70 for application to the direction control 74 in the motor stop 72. The direction control 74 selects a direction for the application of power to the motor 52 through a switch which reverses polarity, the polarity being automatically reversible at the end of a scan in one direction or being setable manually. The scan control 70 also applies signals to the remote chart circuit and the event mark circuits 78 and 80 for application to the monitor 42 to drive charts so that the chart record is independent of changes made in the scanning speed.

The carriage is driven by a feedback loop which includes a tachometer on the motor 52 which moves a disc causing the optical sensor 50 to generate signals for application to a frequency-to-current converter 54. This converter applies current to the summing node 62 related to the speed of the motor. The set speed of the motor from the speed set point 82 is converted in the voltage-to-current converter 60 to current for application to the summing node 62.

The error signals from the null point are amplified by the servo amplifier 64 and applied to motor drive circuit 66 to drive the motor at the preset speed. To reverse direction of the motor stop 72 includes a flip-flop which is switched automatically by push-button switches at the end of a scan or energized manually. It applies a current to the summing node 62 which brings the motor to a stop by causing the drive amplifiers to terminate power for driving the motor. It also initiates a signal to switch the armature switch so that, upon restarting, the motor rotates in the reverse direction to move the carriage back to its starting point.

During the motion of the carriage, light from the halogen lamp 26 is transmitted through apertures in the aperture plate 28 aligned with the bands in the gel with the apertures being smaller in size than the bands and approximately 0.15 millimeter wide in the direction of motion and 3.3 millimeters long in a direction perpendicular to the direction of motion of the slab.

The light passes through the aperture plate 28 (FIG. 1) and the gel slab 14. On the other side of the gel slab 14 the light is received through an aperture plate 18 having an aperture the same size as that in the plate 28. It is possible to mount the optical system on one side of the gel holder and refelct the light contacting the bands rather than transmitting the light from one part of the optical system on one side of the gel to a sensing system on the other side. This method is known in the art.

After light has passed through the aperture in the aperture plate 18, at least some of it is transmitted along one path to a sensing system 22 and some to a reference system 24. A beam splitter 20 and an interference filter 30 passes a frequency in the visible range that corresponds to the frequency at which the gel is stained to a photocell 32 in the sensing system 22 and other frequencies are transmitted to a reference photocell 36 and the two compared. In one embodiment, a filter 34 (FIG. 1) passes only infrared light to the reference photocell 36 since infrared light is not absorbed strongly by the gel or bands.

As can be understood from the above description, the gel scanner of this invention has several advantages such as: (1) there is less background noise and it is therefore better able to detect bands; and (2) it has greater linearity.

Although a preferred embodiment of the invention has been described with some particularity, many modifications and variations are possible in the embodiment without deviating from the invention. Therefore, it is to be understood that, within the scope of the appended claims, the invention may be practiced other than as specifically described.

What is claimed is:

1. A method of scanning dyed gel having bands resolved within it comprising the steps of:
    moving the gel and an optical system with respect to each other;
    transmitting light from a source of light through an aperture in an aperture plate having a dimension in the direction of motion of less than 0.5 millimeter and a dimension perpendicular to the direction of motion of less than 10 millimeters;
    receiving light on the other side of the gel through an aperture plate and transmitting only frequencies of light within the visible range and within the absorption spectrum of the bands to a first photocell; and
    transmitting other frequencies of the light passing through the gel to a reference photocell, which other frequencies of light include light only of frequencies not transmitted to the sensing photocell and having a bandwidth of frequencies at least 10 times wider than the bandwidth of frequencies reaching the said first photocell.

2. A method according to claim 1 in which the step of transmitting only frequency of the light within the visible range includes the step of transmitting only light having wavelengths within the range of 400 to 700 nanometers to the sensing photocell.

3. A method according to claim 2 in which the step of transmitting only frequencies of light includes the step of transmitting light through an interference filter.

4. A method in accordance with claim 2 in which the step of transmitting other frequencies of light to a reference photocell includes the step of transmitting light within bandwidth range of 640 nanometers wavelength to 5 microns wavelength.

5. A method in accordance with claim 4 in which the step of transmitting only frequencies of light within the visible range includes the step of transmitting light within the wavelength range of 560 to 630 nanometers.

6. A method according to claim 1 in which the step of transmitting only frequencies of light includes the step of transmitting light through an interference filter.

7. A method in accordance with claim 6 in which the step of transmitting other frequencies of light to a reference photocell includes the step of transmitting light within bandwidth range of 640 nanometers wavelength to 5 microns wavelength.

8. A method in accordance with claim 1 in which the step of transmitting other frequencies of light to a reference photocell includes the step of transmitting light within bandwidth range of 640 nanometers wavelength to 5 microns wavelength.

9. A method in accordance with claim 8 in which the step of transmitting only frequencies of light within the visible range includes the step of transmitting within the wavelength range of 560 to 630 nanometers.

10. A method according to claim 9 in which the step of transmitting only frequencies of light includes the step of transmitting light through an interference filter.

11. A method in accordance with claim 1 in which the step of transmitting only frequencies of light within the visible range includes the step of transmitting 580 nanometers wavelength light.

12. A method according to claim 3 in which the step of transmitting other frequencies of light includes the step of transmitting light through a beam splitter after the light from the source of light passes through the gel; and the step of transmitting only frequencies of light includes the step of reflecting light from the interference filter back to the beam splitter and from the beam splitter to the reference photocell.

13. Gel scanning apparatus comprising:
a gel holder;
an optical system means;
means for moving the gel holder and optical system means with respect to each other;
said optical system means including a source of light, first aperture means, second aperture means, a beam splitter and first and second light paths;
said first aperture means having an aperture with a dimension in a direction of motion of the gel with respect to the optical system of less than 0.5 millimeter and a dimension in a direction transverse to the direction of motion of less than 10 millimeters;
said source of light an first aperture means being mounted on one side of said gel holder;
said second aperture means being mounted on the other side of gel holder;
said second aperture means having an aperture with a dimension in a direction of motion of less than 0.5 millimeter and in a direction transverse to the direction of motion of less than 10 millimeters;
said beam splitter being positioned to transmit ligth in a first direction along said first light path and light in a second direction along said second light path;
said first light path including a first photodetector means and first-path means for selecting light within a range of 400 nanometers wavelength to 700 nanometers wavelength for application to said first photodetector means;
said second light path having a second photodetector means; and
monitor means for comparing signals from said first and second photodetector means to obtain a signal related to bands in the gel;
said first-path means for selecting light including a filter that passes light within the wavelength range of 400 to 700 nanometers;
said first-path means for selecting being an interference filter; and
second-path means for selecting infrared light in a range of 640 nanometers to 5 microns bandwidth;
said second-path means including a filter for passing infrared light in the range of 640 nanometers to 5 microns bandwidth to said second photodetector means.

14. Apparatus according to claim 13 in which said interference filter has a pass band centered at a wavelength longer than 560 nanometers and shorter than 630 nanometers.

15. Gel scanning apparatus comprising:
a gel holder
an optical system means;
means for moving the gel holder and optical system means with respect to each other;
said optical system means including a source of light, first aperture means, second aperture means, a beam splitter and first and second light paths;
said first aperture means having an aperture with a dimension in a direction of motion of the gel with respect to the optical system of less than 0.5 millimeter and a dimension in a direction transverse to the direction of motion of less than 10 millimeters;
said source of light and first aperture means being mounted on one side of said gel holder;
said second aperture means being mounted on the other side of said gel holder
said second aperture means having an aperture with a dimension in a direction of motion of less than 0.5 millimeter and in a direction transverse to the direction of motion of less than 10 millimeters;
said beam splitter being positioned to transmit light in a first direction along said first light path and light in a second direction along said second light path;
said first light path including a first photodetector means and first-path means for selecting light within a range of 400 nanometers wavelength to 700 nanometers wavelength for application to said first photodetector means;
said second light path having a second photodetector means; and
monitor means for comparing signals from said first and second photodetector means to obtain a signal related to bands in the gel;

said first-path means for selecting being an interference filter; and second-path means for selecting infrared light in a range of 640 nanometers to 5 microns bandwidth; said second-path means including a filter for passing infrared light in the range of 640 nanometers to 5 microns bandwidth to said second photodetector means.

16. Apparatus according to claim 15 in which said interference filter has a pass band center at a wavelength longer than 560 nanometers and shorter than 630 nanometers.

17. Gel scanning apparatus comprising:
a gel holder
an optical system means;
means for moving the gel holder and optical system means with respect to each other;
said optical system means including a source of light, first aperture means, second aperture means, a beam splitter and first and second light paths;
said first aperture means having an aperture with a dimension in a direction of motion of the gel with respect to the optical system of less than 0.5 millimeter and a dimension in a direction transverse to the direction of motion of less than 10 millimeters;
said source of light and first aperture means being mounted on one side of said gel holder;
said second aperture means being mounted on the other side of said gel holder
said second aperture means having an aperture with a dimension in the direction of motion of less than 0.5 millimeter and in a direction transverse to the direction of motion of less than 10 millimeters;
said beam splitter being positioned to transmit light in a first direction along said first light path and light in a second direction along said second light path;
said first light path including a first photodetector means and first-path means for selecting light within a range of 400 nanometers wavelength to 700 nanometers wavelength for application to said first photodetector means;
said second light path having a second photodetector means;
monitor means for comparing signals from said first and second photodetector means to obtain a signal related to bands in the gel; and
second-path means for selecting infrared light in a range of 640 nanometers to 5 microns bandwidth; said second-path means including a filter for passing infrared light in the range of 640 nanometers to 5 microns bandwidth to said second photodetector means.

18. Gel scanning apparatus comprising:
a gel holder;
an optical system means;
means for moving the gel holder and optical system means with respect to each other;
said optical system means including a source of light, first aperture means, second aperture means, a beam splitter and first and second light paths;
said first aperture means having an aperture with a dimension in a direction of motion of the gel with respect to the optical system of less than 0.5 millimeter and a dimension in a direction transverse to the direction of motion of less than 10 millimeters;
said source of light and first aperture means being mounted on one side of said gel holder;
said second aperture means being mounted on the other side of said gel holder
said second aperture means having an aperture with a dimension in a direction of motion of less than 0.5 millimeter and in a direction transverse to the direction of motion of less than 10 millimeters;
said beam splitter being positioned to transmit light in a first direction along said first light path and light in a second direction along said second light path;
said first light path including a first photodetector means and first-path means for selecting light within a range of 400 nanometers wavelength to 700 nanometers wavelength for application to said first photodetector means;
said second light path having a second photodetector means;
monitor means for comparing signals from said first and second photodetector means to obtain a signal related to bands in the gel; and
second-path means for selecting infrared light;
said second-path means for selecting being a filter for passing infrared light in a range of 640 nanometers to 5 microns bandwidth.

19. Gel scanning apparatus comprising:
a gel holder
an optical system means;
means for moving the gel holder and optical system means with respect to each other;
said optical system means including a source of light, first aperture means, second aperture means, a beam splitter and first and second light paths;
said first aperture means having an aperture with a dimension in a direction of motion of the gel with respect to the optical system of less than 0.5 millimeter and a dimension in a direction transverse to the direction of motion of less than 10 millimeters;
said source of light and first aperture means being mounted on one side of said gel holder
said second aperture means being mounted on the other side of said gel holder
said second aperture means having an aperture with a dimension in a direction of motion of less than 0.5 millimeter and in a direction transverse to the direction of motion of less than 10 millimeters;
said beam splitter being positioned to transmit light in a first direction along said first light path and light in a second direction along said second light path;
said first light path including a first photodetector means and first-path means for selecting light within a range of 400 nanometers wavelength to 700 nanometers wavelength for application to said first photodetector means;
said second light path having a second photodetector means; and
monitor means for comparing signals from said first and second detector means to obtain a signal related to bands in the gel;
said first-path means for selecting light including a filter that passes light within the wavelength range of 400 to 700 nanometers; and
said first-path means including means for reflecting light back to said beam splitter, whereby light reflected from said first-path means is transmitted to said second photodetector means.

* * * * *